United States Patent
Kujundžić et al.

[11] Patent Number: 5,629,296
[45] Date of Patent: May 13, 1997

[54] 9A-N-(N'-CARBAMOYL)AND 9A-N-(N'-THIOCARBAMOYL) DERIVATIVES OF 9-DEOXO-9A-AZA-9A-HOMOERYTHROMYCIN A

[75] Inventors: Nedjeliko Kujundžić ; Gabrijela Kobrehel; Željko Kelnerić, all of Zagreb, Croatia

[73] Assignee: Pliva farmaceutiska, kemijska, prehrambena i kozmeticka industrija, dionicko drustvo Zagreb, Zagreb, Croatia

[21] Appl. No.: 350,990

[22] Filed: Nov. 29, 1994

[30] Foreign Application Priority Data

Dec. 8, 1993 [HR] Croatia ................................. P931480A

[51] Int. Cl.$^6$ ........................... A61K 31/70; C07H 17/08
[52] U.S. Cl. ............................. 514/29; 536/7.2; 536/7.4; 536/18.5
[58] Field of Search ................... 536/7.2, 7.4, 18.5; 514/25

[56] References Cited

U.S. PATENT DOCUMENTS 4,464,527  8/1984  Bright ........................................ 536/7.4
4,826,820  5/1989  Brain ........................................... 514/29

*Primary Examiner*—Elli Peselev
*Attorney, Agent, or Firm*—Pollock, Vande Sande & Priddy

[57] ABSTRACT

The invention relates to 9a-N-(N'-carbamoyl) and 9a-N-(N'-thiocarbamoyl) derivatives of 9-deoxo-9a-aza-9a-homoerythromycin A, novel semisynthetic macrolide antibiotics of the azalide series, of the formula (I)

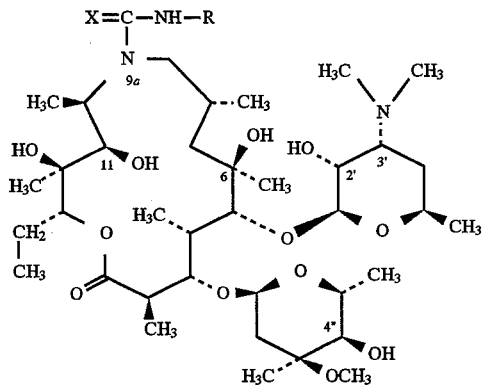

wherein R represents a $C_1$–$C_3$ alkyl, aryl or aralkyl group and X represents O or S, and pharmaceutically acceptable addition salts thereof with inorganic or organic acids, to the intermediates and processes for the preparation thereof, to a process for the preparation of pharmaceutical compositions as well as to the use of pharmaceutical compositions in the treatment of bacterial infections.

17 Claims, No Drawings

9A-N-(N'-CARBAMOYL) AND 9A-N-(N'-THIOCARBAMOYL) DERIVATIVES OF 9-DEOXO-9A-AZA-9A-HOMOERYTHROMYCIN A

The present invention relates to 9a-N-(N'-carbamoyl) and 9a-N-(N'-thiocarbamoyl) derivatives of 9-deoxo-9a-aza-9a-homoerythromycin A, novel semisynthetic macrolide antibiotics of the azalide series having an antibacterial action of the general formula (I)

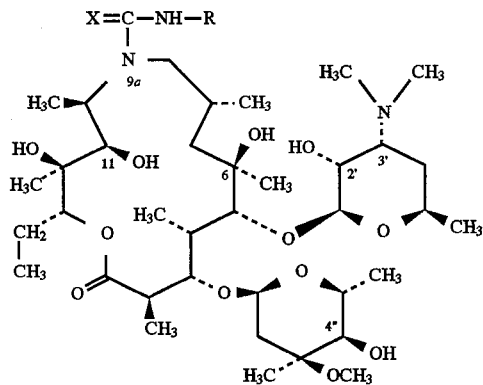

wherein R represents a $C_1$–$C_3$ alkyl, aryl or aralkyl group and X represents O or S, to pharmaceutically acceptable addition salts thereof with inorganic or organic acids, to a process for the preparation thereof, to a process for the preparation of the pharmaceutical compositions as well as to the use of pharmaceutical compositions obtained in the treatment of bacterial infections.

Erythromycin A is a macrolide antibiotic, whose structure is characterized by a 14-member macrolactone ring having a carbonyl group in C-9 position. It was found by McGuire in 1952 (Antibiot. Chemother., 1952; 2:281) and for over 40 years it has been considered as a reliable and effective antimicrobial agent in the treatment of diseases caused by Gram-positive and some Gram-negative microorganisms. However, in an acidic medium it is easily converted into anhydroerythromycin A, an inactive C-6/C-12 metabolite of a spiroketal structure (Kurath P. et al., Experientia 1971; 27:362). It is well-known that spirocyclisation of aglycone ring of erythromycin A is successfully inhibited by a chemical transformation of C-9 ketones or hydroxy groups in a C-6 and/or C-12 position. By the oximation of C-9 ketones (Djokić S. et al., Tetrahedron Lett., 1967; 1945) and by subsequently modifying the obtained 9(E)-oxime into 9-[O-(2-methoxyethoxy)-methyloxime] erythromycin A (ROKSITROMICIN) (Ambrieres, G. S., FR 2,473,525/1981) or 9(S)-erythromycylamine (Egan R. S. et al., J. Org. Chem., 1974; 39:2492) or a more complex oxazine derivative thereof, 9-deoxo-11-deoxy-9,11-{imino[2-(2-methoxyethxyethylidene]-oxy}-9(S)-erythromycin A (DIRITROMICIN) (Lugar P. et al., J. Crist. Mol. Struct., 1979; 9:329), novel semisynthetic macrolides were synthetized, whose basic characteristic, in addition to a greater stability in an acidic medium, is a better pharmacokinetics and a long half-time with regard to the parent antibiotic erythromycin A. In a third way for modifying C-9 ketones use is made of Beckmann rearrangement of 9(E)-oxime and of a reduction of the obtained imino ether (Kobrehel G. et al., U.S. Pat. No. 4,328,334, 5/1982) into 11-aza-10-deoxo-10-dihydroerythromycin A (9-deoxo-9a-aza-9a-homoerythromycin A) under broadening the 14-member ketolactone ring into a 15-member azalactone ring. By reductive N-methylation of 9a-amino group according to Eschweiler-Clark process (Kobrehel G. et al., BE Pat. No. 892,357, 7/1982) or by a preliminary protection of amino group by means of conversion into the corresponding N-oxides and then by alkylation and reduction (Bright G. M., U.S. Pat. No. 4,474,768, 10/1984) N-methyl-11-aza-10-deoxo-10-dihydroerythromycin A (9-deoxo-9a-methyl-9a-aza-9a-homoerythromycin A, AZITROMICIN) was synthetized, a prototype of azalide antibiotics, which, in addition to a broad antimicrobial spectrum including Gram-negative bacteria and intracellular microorganisms, are characterized by a specific mechanism of transport to the application site, a long biological half-time and a short therapy period. In EPA 0 316 128 (Bright G. M.) novel 9a-allyl and 9a-propargyl derivatives of 9-deoxo-9a-aza-9a-homoerythromycin A are disclosed and in U.S. Pat. No. 4,492,688, 1/1985 (Bright G. M.) the synthesis and the antibacterial activity of the corresponding cyclic ethers are disclosed. In the Croatian patent application 381-03/93-05/041 (559-93-1) there are further disclosed the synthesis and the activity spectrum of novel 9-deoxo-9a-aza-11-deoxy-9a-homoerythromycin A 9a,11-cyclic carbamates and O-methyl derivatives thereof.

According to the known and established Prior Art, 9a-N-(N'-carbamoyl) and 9a-N-(N'-thiocarbamoyl) derivatives of 9-deoxo-9a-aza-9a-homoerythromycin A and pharmaceutically acceptable addition salts thereof with inorganic or organic acids, a process for the preparation thereof as well as the preparation methods and use an pharmaceutical preparations have not been disclosed as yet.

It has been found and it is an object of the present invention that 9a-N-(N'-carbamoyl) and 9a-N-(N'-thiocarbamoyl) derivatives of 9-deoxo-9a-aza-9a-homoerythromycin A, novel semisynthetic macrolide antibiotics of the azalide series and pharmaceutically acceptable addition salts thereof with inorganic or organic acids may be prepared by reacting 9-deoxo-9a-aza-9a-homoerythromycin A with isocyanates or isothiocyanates and optionally by reacting the obtained 9a-N-(N'-carbamoyl) and 9a-N-(N'-thiocarbamoyl) derivatives of 9-deoxo-9a-aza-9a-homoerythromycin A with inorganic and organic acids.

It has been found that novel 9a-N-(N'-carbamoyl) and 9a-N-(N'-thiocarbamoyl) derivatives of 9-deoxo-9a-aza-9a-homoerythromycin A of the formula (I)

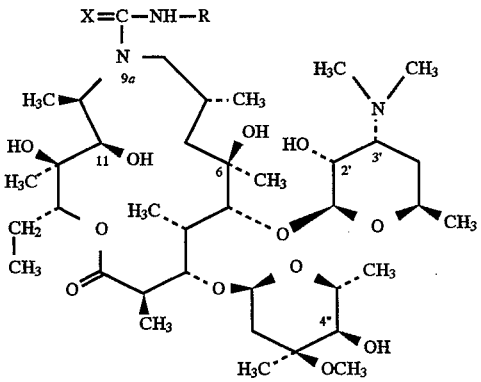

wherein R represents a $C_1$–$C_3$ alkyl, aryl or aralkyl group and X represents O or S, and pharmaceutically acceptable addition salts thereof with inorganic or organic acids may be prepared by reacting 9-deoxo-9a-aza-9a-homoerythromycin A with isocyanates or isothiocyanates of the general formula (II)

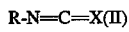

wherein R and X have the above meanings, in toluene, xylene or some other aprotic solvent, at a temperature of 20° to 110° C., the isocyanates of the general formula (II) wherein R represents a phenyl group, 1-naphthyl group or unsubstituted or substituted aromatic 5-member and 6-member rings having one or two hetero atoms being prepared in situ by means of Curtius rearrangement of the corresponding acid azide at elevated temperature.

Pharmaceutically acceptable acid addition salts, which also represent an object of the present invention, are obtained by reacting 9a-N-(N'-carbamoyl) and 9a-N-(N'-thiocarbamoyl) derivatives of 9-deoxo-9a-aza-9a-homoerythromycin A with an at least equimolar amount of the corresponding inorganic or organic acid such as hydrochloric acid, hydroiodic acid, sulfuric acid, phosphoric acid, acetic acid, trifluoroacetic acid, propionic acid, benzoic acid, benzene sulfonic acid, methane sulfonic acid, lauryl sulfonic acid, stearic acid, palmitic acid, succinic acid, ethylsuccinic acid, lactobionic acid, oxalic acid, salicylic acid and similar acids, in a solvent inert to the reaction. Addition salts are isolated by evaporating the solvent or, alternatively, by filtration after a spontaneous precipitation or a precipitation by the addition of a non-polar cosolvent.

9a-N-(N'-carbamoyl) and 9a-N-(N'-thiocarbamoyl) derivatives of 9-deoxo-9a-aza-9a-homoerythromycin A of the formula (I) and pharmaceutically acceptable addition salts with inorganic or organic acids thereof possess an antibacterial activity in vitro. Minimum inhibitory concentrations (MIC, mcg/ml) are determined by dilution method on microplates according to the recommendation of National Committee for Clinical Laboratory Standards (NCCLS, M7-A2). It is evident from Table 1 that standard strains and clinical isolates tested are susceptible to newly synthetised compounds. Thus they may be used for disinfection of rooms, chirurgical instruments and humans and as therapeutic agents in the treatment of infective diseases in animals, especially mammals and humans, caused by a broad spectrum of Gram-positive bacteria, mycoplasmas and generally patogenic microorganisms that are susceptible to the compounds of the formula (I). To this purpose the above compounds and pharmaceutically acceptable acid addition salts thereof may be administered orally in usual doses from 0.2 mg/kg body weight daily to about 250 mg/kg/day, most preferably from 5–50 mg/kg/day, or parenterally in the form of subcutaneous and intramuscular injections.

TABLE 1

Antibacterial in vitro activity of novel 9a-N-(N'-carbamoyl) and 9a-N-(N'-thiocarbamoyl) derivatives of 9-deoxo-9a-aza-9a-homoerythromycin A in comparison with the starting amine

| Test organism | MIC (mcg/ml) | | | | | |
|---|---|---|---|---|---|---|
| | 9a-NH* | 1 | 4 | 5 | 6 | 7** |
| Staphylococcus epidermidis ATCC 12228 | 3.12 | 6.25 | 25.0 | 3.12 | 6.25 | 6.25 |
| Staphylococcus aureus ATCC 6538P | 3.12 | 1.56 | 12.5 | 6.25 | 3.12 | 3.12 |
| Micrococcus flavus ATCC 10240 | 1.56 | 3.12 | 12.5 | 3.12 | 3.12 | 1.56 |
| Streptococcus faecalis ATCC 8043 | 3.12 | 3.12 | 6.25 | 3.12 | 3.12 | 3.12 |
| Bacillus subtilis NCTC 8236 | 12.5 | 1.56 | 25.0 | 6.25 | 3.12 | 1.56 |

TABLE 1-continued

Antibacterial in vitro activity of novel 9a-N-(N'-carbamoyl) and 9a-N-(N'-thiocarbamoyl) derivatives of 9-deoxo-9a-aza-9a-homoerythromycin A in comparison with the starting amine

| Test organism | MIC (mcg/ml) | | | | | |
|---|---|---|---|---|---|---|
| | 9a-NH* | 1 | 4 | 5 | 6 | 7** |
| B. pumilus NCTC 8241 | 12.5 | 6.25 | 12.5 | 6.25 | 3.12 | 1.56 |
| B. cererus ATCC 11778 | 3.12 | 6.25 | 12.5 | 12.5 | 6.25 | 6.25 |
| Pseudomonas aeruginosa NCTC 10490 | 25.0 | 25.0 | 50.0 | 50.0 | 50.0 | 50.0 |
| Esherichia coli ATCC 10536 | 3.12 | 12.5 | 12.5 | 12.5 | 25.0 | 12.5 |
| Salmonella Panama 6117 | 3.12 | 6.25 | 25.0 | 25.0 | >100.0 | >100.0 |
| BHS-A Streptococcus pyogenes J-21 | 3.12 | | 12.5 | 3.12 | | |
| BHS-B Streptococcus Agalactiae J-22 | 1.56 | | 12.5 | 1.56 | | |

*9-deoxo-9a-aza-9a-homoerythromycin A
**numbers designate newly synthetised compounds from the corresponding Examples Process for the preparation of 9a-N-(N'-carbamoyl) and 9a-N-(N'-thiocarbamoyl) derivatives of 9-deoxo-9a-aza-9a-homoerythromycin A of this invention is illustrated by the following Examples which should in no way be construed as a limitation of the scope thereof.

EXAMPLE 1

9-deoxo-9a-N-(N'-isopropyl-carbamoyl)-9a-aza-9a-homoerythromycin A

A mixture of 9-deoxo-9a-aza-9a-homoerythromycin A (7.27 g; 0.01 mole), isopropylisocyanate (0.94 g; 0.011 mole) and toluene (40 ml) was stirred for 1 hour at the temperature of 30° C. The reaction mixture was evaporated at reduced pressure (40° C.) to dryness to give crude 9-deoxo-9a-N-(N'-isopropyl-carbamoyl)-9a-aza-9a-homoerythromycin A (7.0 g; 86.2%), m.p. 128°–136° C. By recrystallization of the obtained product from a methanol-water mixture a chromatographically homogenous substance having the following physico-chemical constants was obtained:

m.p. 135°–144° C.

TLC, EtAc-(n-$C_6H_6$)-$NHEt_2$ (100:100:20), Rf 0.351.

$CHCl_3$—$CH_3OH$-conc. $NH_4OH$ (6:1:0.1), Rf 0.553.

IR (KBr) $cm^{-1}$ 1730, 1625, 1515, 1455, 1380, 1270, 1165, 1050, 950.

$^1$H NMR (300 MHz, $CDCl_3$)δ 5.00 (1H, H-13), 4.85 (1H, H-1"), 4.47 (1H, H-1'), 4.02 (1H, H-3), 3.91 (1H, — CH($CH_3$)$_2$), 3.50 (1H, H-5), 3.43 (1H, H-9a), 3.28 (3H, 3"-$OCH_3$), 2.49 (1H, H-9b), 2.32 [6H, 3'-N($CH_3$)$_2$, 2.31 (1H, H-8), 1.62 (1H, H-7a), 1.29 (3H, 10-$CH_3$), 1.14 [6H, —CH($CH_3$)$_2$], 1.13 (1H, H-7b), 1.04 (3H, 8-$CH_3$).

$^{13}$C NMR (75 MHz, $CDCl_3$)δ (175.5 (C-1), 158.2 (9a-N CONH), 103.8 (C-1'), 96.0 (C-1"), 87.9 (C-5), 78.8 (C-3), 48.8 (3"-$OCH_3$), 45.5 (C-2), 42.2 [—CH($CH_3$)$_2$], 39.9 [3'-N($CH_3$)$_2$], 27.4 (C-8), 22.9 [—CH($CH_3$)$_2$, 20.5 (8-$CH_3$), 12.2 (10-$CH_3$).

EXAMPLE 2

9-deoxo-9a-N-{N'-[(4-methyl-5-oxazole)-carbamoyl]}-9a-aza-9a-homoerythromycin A A mixture of 9-deoxo-9a-aza-9a-homoerythromycin A (4.8 g; 0.0065 mole), 4-methyl-5-oxazole-carboxylic acid azide (1.0 g; 0.0066 mole) and dry toluene (30 ml) was heated for 15 minutes at the boiling temperature and then, by distillation at reduced pressure (40° C.), evaporated to dryness. The obtained residue was suspended in acetone (20 ml), stirred at room temperature and then the obtained crystals were filtered to give 9-deoxo-9a-N-{N'-[(4-methyl-5-oxazole)-carbamoyl]}-9a-aza-9a-homoerythromycin A (5.4 g; 93.3%), m.p. 174°–177° C. By recrystallization from hot acetone, a chromatographically homogenous product having the following physico-chemical constants was obtained:

m.p. 181°–183° C.

TLC, EtAc-(n-$C_6H_6$)-$NHEt_2$ (100:100:20), Rf 0.149.

$CHCl_3$—$CH_3OH$-conc. $NH_4OH$ (6:1:0.1), Rf 0.491.

IR (KBr) $cm^{-1}$ 1730, 1680, 1655, 1490, 1460, 1380, 1170, 1050, 755, 660.

$^1H$ NMR (300 MHz, Py $d_5$, 50° C.)δ 9.02 (9a-N-CONH), 7.95 (—CH=N) 5.71 (1H, H-13), 5.15 (1H, H-1"), 4.94 (1H, H-1'), 4.77 (1H, H-3), 4.07 (1H, H-5), 3.96 (1H, H-9a), 3.44 (3H, 3"-$OCH_3$), 2.50 (1H, H-9b), 2.32 [6H, 3'-N($CH_3$)$_2$], 2.34 (1H, H-8), 2.35 (1H, H-7a), 1.68 (3H, 10-$CH_3$), 1.97 (1H, H-7b), 1.09 (3H, 8-$CH_3$).

$^{13}C$ NMR (75 MHz, Py $d_5$, 50° C.)δ 177.2 (C-1), 157.2 (9a-NCONH), 104.2 (C-1'), 96.9 (C-1"), 86.6 C-5), 80.5 (C-3), 50.1 (3"-$OCH_3$), 46.5 (C-2), 42.2 (C-4), 41.0 [3"-N($CH_3$)$_2$], 29.1 (C-8), 21.2 (8-$CH_3$), 14.1 (10-$CH_3$), 149.9, 142.2, 128.2 and 12.2 (4-methyl-5-oxazole).

EXAMPLE 3

9-deoxo-9a-N-[N'-(2-furyl)-carbamoyl]-9a-aza-9a-homoerythromycin A

Analogously to the process disclosed in Example 2, from 9-deoxo-9a-aza-9a-homoerythromycin A (2.18 g; 0.003 mole), 2-furancarboxylic acid azide (0.5 g, 0.0036 mole) and toluene (15 ml) a resinous residue (2.1 g) was obtained, wherefrom by chromatography on a silica gel column using the solvent system $CHCl_3$—$CH_3OH$ (7:3) 9-deoxo-9a-N-[N'-(2-furyl)-carbamoyl]-9a-aza-9a-homoerythromycin A (1.7 g; 77.0%) having the following physico-chemical constants was obtained:

m.p. 155°–159° C.

TLC, EtAc-(n-$C_6H_6$)-$NHEt_2$ (100:100:20), Rf 0.262.

$CHCl_3$—$CH_3OH$-conc. $NH_4OH$ (6:1:0.1), Rf 0.574.

IR ($CHCl_3$) $cm^{-1}$ 1730, 1655, 1520, 1460, 1380, 1270, 1165, 1050, 1000, 955, 900, 830, 730.

$^1H$ NMR (300 MHz, DMSO)δ 8.51 (9a-N-CONH), 7.24 (—O—CH=) 6.34 (—O—CH=CH—), 6.00 (—CH=C—NH), 5.04 (1H, H-13), 4.77 (1H, H-1"), 4.47 (1H, H-1'), 4.01 (1H, H-3), 3.42 (1H, H-5), 3.47 (1H, H-9a), 3.35 (3H, 3'-$OCH_3$), 3.25 (1H, H-9b), 2.50 [6H, 3'-N($CH_3$)$_2$], 2.07 (1H, H-8), 1.45 (1H, H-7a), 1.20 (1H, H-7b), 1.15 (3H, 10-$CH_3$), 0.90 (3H, 8-$CH_3$).

$^{13}C$ NMR (75 MHz, DMSO)δ 175.5 (C-1), 155.4 (9a-NCONH), 101.9 (C-1'), 95.3 (C-1"), 84.4 (C-5), 78.6 (C-3), 48.8 (3"-$OCH_3$), 44.6 (C-2), 40.0 (C-4), 40.1 [3'-N($CH_3$)$_2$], 27.7 (C-8), 19.7 (8-$CH_3$), 13.2 (10-$CH_3$), 147.7, 136.5, 118.9, 98.0 (5-furanoyl).

EXAMPLE 4

9-deoxo-9a-N-[N'-(4-pyridyl)-carbamoyl]-9a-aza-9a-homoerythromycin A

Analogously to the process disclosed in Example 2, from 9-deoxo-9a-aza-9a-homoerythromycin A (2.18 g; 0.003 mole), isonicotinic acid azide (0.53 g, 0.0036 mole) and toluene (15 ml) a resinous residue (2.26 g) was obtained, wherefrom by recrystallization from a methanol-water mixture 9-deoxo-9a-N-[N'-(4-pyridyl)-carbamoyl]-9a-aza-9a-homoerythromycin A (1.9 g; 74.8%) having the following physico-chemical constants was obtained:

m.p. 149°–153° C.

TLC, EtAc-(n-$C_6H_6$)-$NHEt_2$ (100:100:20), Rf 0.089.

$CHCl_3$—$CH_3OH$-conc. $NH_4OH$ (6:1:0.1), Rf 0.441.

IR ($CHCl_3$) $cm^{-1}$ 1730, 1650, 1590, 1510, 1460, 1380, 1330, 1280, 1165, 1050, 1000, 955, 900, 830, 730.

$^1H$ NMR (300 MHz, DMSO)δ 8.66 (9a-N—CONH), 8.25, 7.35 (4-piridyl), 5.16 (1H, H-13), 4.89 (1H, H-1"), 4.52 (1H, H-1'), 4.15 (1H, H-3), 3.53 (1H, H-5), 3.51 (1H, H-9a), 3.33 (3H, 3"-$OCH_3$), 3.28 (1H, H-9b), 2.34 [6H, 3'-N($CH_3$)$_2$], 2.28 (1H, H-8), 1.62 (1H, H-7a), 1.23 (1H, H-7b), 1.36 (3H, 10-$CH_3$), 1.04 (3H, 8-$CH_3$).

$^{13}C$ NMR (75 MHz, DMSO)δ 176.1 (C-1), 155.5 (9a-N CONH), 102.2 (C-1'), 95.5 (C-1"), 84.3 (C-5), 78.7 (C-3), 48.9 (3"-$OCH_3$), 44.8 (C-2), 40.2 (C-4), 40.4 [3'-N($CH_3$)$_2$], 27.8 (C-8), 20.2 (8-$CH_3$), 14.4 (10-$CH_3$), 149.8, 148.0, 113.9 (4-pyridyl).

EXAMPLE 5

9-deoxo-9a-N-(N'-phenyl-carbamoyl)-9a-aza-9a-homoerythromycin A

Analogously to the process disclosed in Example 2, from 9-deoxo-9a-aza-9a-homoerythromycin A (2.0 g; 0.0027 mole), benzoic acid azide (0.5 g, 0.0034 mole) and toluene (15 ml) a resinous residue (2.43 g) was obtained, wherefrom by chromatography on a silica gel column using a solvent system $CH_2Cl_2$—$CH_3OH$ (85:15), 9-deoxo-9a-N-(N'-phenyl-carbamoyl)-9a-aza-9a-homoerythromycin A (1.4 g; 61.4%) having the following physico-chemical constants was obtained:

m.p. 126°–130° C.

TLC, EtAc-(n-$C_6H_6$)-$NHEt_2$ (100:100:20), Rf 0.345.

$CHCl_3$—$CH_3OH$-conc. $NH_4OH$ (6:1:0.1), Rf 0.637.

IR (KBr) $cm^{-1}$ 1730, 1645, 1600, 1539, 1510, 1455, 1380, 1315, 1240, 1165, 1045,950, 895, 755, 690.

$^1H$ NMR (300 MHz, DMSO)δ 8.11 (9a-N—CONH), 7.30, 7.35 (phenyl), 5.05 (1H, H-13), 4.79 (1H, H-1"), 4.46 (1H, H-1'), 4.04 (1H, H-3), 3.46 (1H, H-5), 3.28 (1H, H-9a), 3.23 (3H, 3"-$OCH_3$), 3.16 (1H, H-9b), 2.34 [6H, 3'-N($CH_3$)$_2$], 2.16 (1H, H-8), 1.58 (1H, H-7a), 1.15 (1H, H-7b), 1.25 (3H, 10-$CH_3$), 0.90 (3H, 8-$CH_3$).

$^{13}C$ NMR (75 MHz, DMSO)δ 175.6 (C-1), 156.1 (9a-N CONH), 102.0 (C-1'), 95.4 (C-1"), 84.4 (C-5), 78.5 (C-3), 48.9 (3"-$OCH_3$), 44.6 (C-2), 39.4 (C-4), 40.1 [3'-N($CH_3$)$_2$], 27.3 (C-8), 20.0 (8-$CH_3$), 14.0 (10-$CH_3$), 140.6, 127.9 and 114.4 (phenyl).

EXAMPLE 6

9-deoxo-9a-N-(N'-benzyl-carbamoyl)-9a-aza-9a-homoerythromycin A

Analogously to the process disclosed in Example 1, from 9-deoxo-9a-aza-9a-homoerythromycin A (7.27 g; 0.01 mole), benzylisocyanate (1.33 g, 0.01 mole) and toluene (15 ml) a resinous residue (8.4 g) was obtained, wherefrom by chromatography on a silica gel column using a solvent system $CHCl_3$—$CH_3OH$ (7:3), 9-deoxo-9a-N-(N'-benzyl-carbamoyl)-9a-aza-9a-homoerythromycin A (6.5 g, 75.6%) having the following physico-chemical constants was obtained:

m.p. 142°–144° C.

TLC, EtAc-(n-$C_6H_6$)-$NHEt_2$ (100:100:20), Rf 0.355.

$CHCl_3$—$CH_3OH$-conc. $NH_4OH$ (6:1:0.1), Rf 0.621.

IR (KBr) $cm^{-1}$ 1730, 1630, 1525, 1410, 1380, 1270, 1165, 1045, 950, 895, 755, 700.

$^1H$ NMR (300 MHz, $CDCl_3$)δ 7.30, 5.00, 4.40 (—$CH_2$—$C_6H_5$), 5.04 (1H, H-13), 4.83 (1H, H-1"), 4.48 (1H, H-1'), 4.00 (1H, H-3), 3.52 (1H, H-5), 3.48 (1H, H-9a), 3.28 (3H, 3"-$OCH_3$), 2.51 (1H, H-9b), 2.56 [6H, 3'-N($CH_3$)$_2$], 2.34 (1H, H-8), 1.66 (1H, H-7a), 1.10 (1H, H-7b), 0.99 (3H, 10-$CH_3$), 1.36 (3H, 8-$CH_3$). $^{13}C$ NMR (75 MHz, $CDCl_3$)δ 175.7 (C-1), 159.3 (9a-N$\underline{C}$ONH), 103.8 (C-1'), 96.5 (C-1"), 88.8 (C-5), 78.8 (C-3), 48.9 (3"-$OCH_3$), 45.9 (C-2), 40.4 (C-4), 40.2 [3'-N($CH_3$)$_2$], 27.3 (C-8), 20.5 (8-$CH_3$), 12.3 (10-$CH_3$), 139.1, 128.3, 127.2 and 126.8, 45.9 (—$CH_2$—$C_6H_5$).

EXAMPLE 7

9-deoxo-9a-N-(N'-benzyl-thiocarbamoyl)-9a-aza-9a-homoerythromycin A

Analogously to the process disclosed in Example 1, from 9-deoxo-9a-aza-9a-homoerythromycin A (7.27 g; 0.01 mole), benzylisothiocyanate (1.50 g, 0.01 mole) and toluene (30 ml) under stirring of the reaction mixture for 8 hours at the temperature of 30° C., a resinous residue (8.6 g) was isolated, wherefrom by chromatography on a silica gel column using the solvent system $CHCl_3$—$CH_3OH$ (7:3), 9-deoxo-9a-N-(N'-benzyl-thiocarbamoyl)-9a-aza-9a-homoerythromycin A (7.2 g; 82.1%) having the following physico-chemical constants was obtained:

m.p. 119°–122° C.

TLC, EtAc-(n-$C_6H_6$)-$NHEt_2$ (100:100:20), Rf 0.370.

$CHCl_3$—$CH_3OH$-conc. $NH_4OH$ (6:1:0.1), Rf 0.689.

IR (KBr) $cm^{-1}$ 1730, 1630, 1525, 1410, 1380, 1270, 1165, 1045, 950, 895, 755, 700.

$^1H$ NMR (300 MHz, $CDCl_3$)δ 7.36, 4.85, 4.72 (—$CH_2$—$C_6H_5$), 4.75 (1H, H-13), 4.87 (1H, H-1"), 4.4 (1H, H-1'), 4.10 (1H, H-3), 3.81 (1H, H-11), 3.49 (1H, H-5), 3.30 (3H, 3"-$OCH_3$), 3.03 (1H, H-4"), 2.34 [6H, 3'-N($CH_3$)$_2$], 2.31 (1H, H-8), 1.52 (1H, H-7a), 1.26 (1H, H-7b), 1.31 (3H, 10-$CH_3$), 0.96 (3H, 8-$CH_3$).

EXAMPLE 8

9-deoxo-9a-N-[N'-(1-naphthyl)-carbamoyl]-9a-aza-9a-homoerythromycin A

Analogously to the process disclosed in Example 1, from 9-deoxo-9a-aza-9a-homoerythromycin A (7.27 g; 0.01 mole), 1-naphthylisocyanate (1.7 g, 0.01 mole) and toluene (40 ml) by stirring the reaction mixture for 1 hour at the temperature of 20° C. a resinous residue (9.0 g) was isolated, wherefrom by chromatography on a silica gel column using the solvent system $CHCl_3$—$CH_3OH$-conc. $NH_4OH$ (6:1:0.1) 9-deoxo-9a-N-[N'-(1-naphthyl)-carbamoyl]-9a-aza-9a-homoerythromycin A (7.8 g; 86.6%) having the following physico-chemical constants was obtained:

m.p. 134°–137° C.

TLC, EtAc-(n-$C_6H_6$)-$NHEt_2$ (100:100:20), Rf 0.335.

$CHCl_3$—$CH_3OH$-conc. NH4OH (6:1:0.1), Rf 0.658.

IR ($CHCl_3$) $cm^{-1}$ 1740, 1635, 1530, 1500, 1455, 1380, 1340, 1265, 1160, 1050, 1010, 960, 890, 795, 775, 735; 700.

We claim:

1. A compound of the general formula (I)

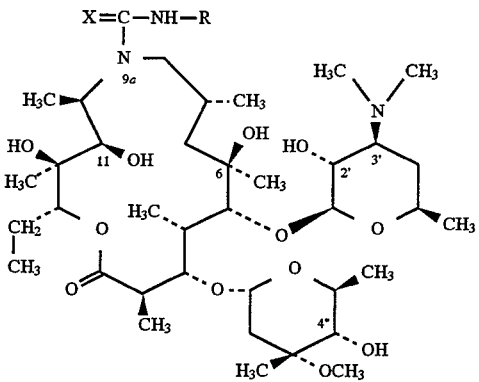

wherein

R is a $C_1$-$C_3$ alkyl, or

R is a mono- or bicyclic aryl group of up to 10 carbon atoms, or

R is an aralkyl wherein aryl group of said aralkyl is a mono- or bicyclic aromatic hydrocarbon of up to 10 carbon atoms and the alkyl group of said aralkyl contains 1 carbon atom, or R is unsubstituted or substituted 5- to 6-membered heterocyclic group containing one or two hetero atoms wherein said hetero atom is N or O, or both and X is O or S, and a pharmaceutically acceptable addition salt with an acid selected from the group consisting of inorganic acid and organic acid.

2. The compound according to claim 1, wherein R is a $C_1$-$C_3$ alkyl, and X is O.

3. The compound according to claim 2, wherein said $C_1$-$C_3$ alkyl group is an isopropyl group.

4. The compound according to claim 3, wherein R is a mono- or bicyclic aryl group of up to 10 carbon atoms and X is O.

5. The compound according to claim 4, wherein said aryl group is phenyl.

6. The compound according to claim 4, wherein said aryl group is 1-naphtyl.

7. The compound according to claim 1, wherein R is an unsubstituted or substituted 5- to 6-membered heteroaryl group containing one or two hetero atoms wherein said hetero atoms is O or N or both, and wherein said heteroaryl is substituted by a $C_1$-$C_3$ alkyl, and X is O.

8. The compound according to claim 7, wherein said heteroaryl group represents 4-methyl-5-oxazoyl group.

9. The compound according to claim 7, wherein said heteroaryl group represents furyl group.

10. The compound according to claim 7, wherein said heteroaryl group represents 4-pyridyl group.

11. The compound according to claim 1, wherein R is an aralkyl wherein said aryl is a mono- or bicyclic aromatic hydrocarbon of up to 10 carbon atoms and said alkyl contains up to 3 carbon atoms and X represents O.

12. The compound according to claim 11, wherein said aralkyl group represents benzyl group.

13. The compound according to claim 1, wherein R is an aralkyl wherein aryl is a mono- or bicyclic aromatic hydrocarbon of up to 10 carbon atoms and said alkyl contains up to 3 carbon atoms and X represents S.

14. The compound according to claim 13, wherein said aralkyl group represents benzyl group.

15. A process for preparation of the compound of the general formula (I)

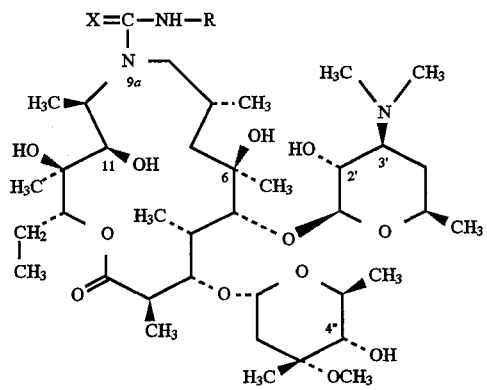

wherein

R is a $C_1$–$C_3$ alkyl, or

R is a mono- or bicyclic aryl group of up to 10 carbon atoms, or

R is an aralkyl wherein aryl portion of said aralkyl is a mono- or bicyclic aromatic hydrocarbon of up to 10 carbon atoms and the portion of said aralkyl contains 1 carbon atom, or R is unsubstituted or substituted 5- to 6-membered heterocyclic group containing one or two hetero atoms wherein said hetero atom is N or O, or both and X is O or S, and their pharmaceutically acceptable addition salt with inorganic or organic acid, characterized in that 9-deoxo-9a-aza-9a-homoerythromycin A is reacted with isocyanates or isothiocyanates of the general formula (II)

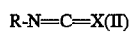

wherein R and X have the meaning as defined above, in an aprotic solvent selected from the group consisting of toluene and xylene, at a temperature from 20° to 100° C., characterized in that the compounds of the general formula (II) wherein R represents aryl or heteroaryl group as defined above and X represents O being prepared in situ by means of Curtius rearrangement of the corresponding acid azide at elevated temperature, which are then optionally subjected to reaction with inorganic acid or organic acid to give corresponding acid addition salt.

16. A pharmaceutical composition useful for treating bacterial infections in humans and animals which comprises an antibacterially effective amount of the compound of the formula (I) or a pharmaceutically acceptable acid addition salt thereof:

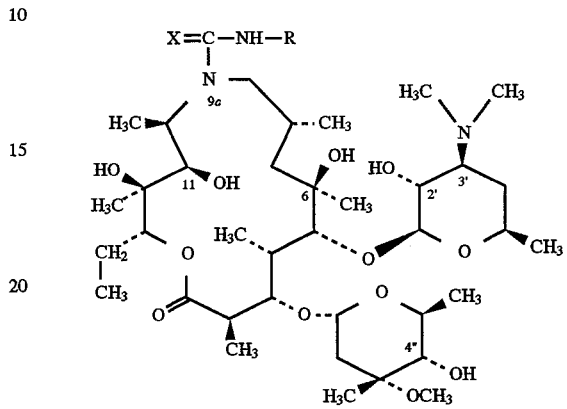

wherein

R is a $C_1$–$C_3$ alkyl, or

R is a mono- or bicyclic aryl group of up to 10 carbon atoms, or

R is an aralkyl wherein aryl group of said aralkyl is a mono- or bicyclic aromatic hydrocarbon of up to 10 carbon atoms and alkyl group of said aralkyl contains 1 carbon atom, or R is unsubstituted or substituted 5- to 6-membered heterocyclic group containing one or two hetero atoms wherein said hetero atom is N or O, or both and X is O or S, in combination with a pharmaceutically acceptable carrier.

17. A method for treating bacterial infections in humans and animals which comprises administering to a human or animals in need thereof an antibacterially effective amount of the compound of the formula (I) or a pharmaceutically acceptable acid addition salt thereof as claimed in claim 1, in combination with a pharmaceutically acceptable carrier.

* * * * *

UNITED STATES PATENT AND TRADEMARK OFFICE
CERTIFICATE OF CORRECTION

PATENT NO. : 5,629,296
DATED : May 13, 1997
INVENTOR(S) : Kujundzic, et. al.

It is certified that error appears in the above-indentified patent and that said Letters Patent is hereby corrected as shown below:

Title page, item [73], Assignee: should read--Pliva farmaceutska, Kemijska, prehrambena i kozmeticka industrija, dionicko drustvo Zagreb--.

Signed and Sealed this

Twenty-third Day of September, 1997

*Attest:*

BRUCE LEHMAN

*Attesting Officer*    *Commissioner of Patents and Trademarks*